US00PP24962P2

(12) United States Plant Patent
Kordes

(10) Patent No.: US PP24,962 P2
(45) Date of Patent: Oct. 14, 2014

(54) MINIATURE ROSE PLANT NAMED 'KORPOT033'

(50) Latin Name: *Rosa hybrida*
Varietal Denomination: KORpot033

(71) Applicant: Tim-Hermann Kordes, Klein Offenseth-Sparrieshoop (DE)

(72) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 13/986,585

(22) Filed: May 15, 2013

(51) Int. Cl.
*A01H 5/00* (2006.01)

(52) U.S. Cl.
USPC ..... Plt./121

(58) Field of Classification Search
USPC ..... Plt./121
See application file for complete search history.

*Primary Examiner* — Kent L Bell

(57) ABSTRACT

A new and distinct variety of rose with long lasting, novel dark pink flowers, and attractive foliage with good disease resistance. It exhibits upright to bushy growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORpot033'. The new variety of rose plant of the present invention originated from a controlled crossing in a breeding program of two distinct parents during the summer of 2009. The crossing was between an 'un-named seedling', the seed parent, and another 'un-named seedling', the pollen parent by the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORpot033'.

CROSS REFERENCES AND FEDERAL R&D STATEMENT

There are no cross referenced or related applications. This variety was developed without the aid of any research grant.

SUMMARY OF THE INVENTION

The new rose plant may be distinguished from its seed parent, an 'un-named seedling', by the following combination of characteristics:

1. 'KORpot033' has dark pink flowers, whereas the 'un-named seedling' has apricot-orange flowers.
2. 'KORpot033' has medium sized flowers, whereas the 'un-named seedling' has large sized flowers.

The new rose plant may be distinguished from its pollen parent, an 'un-named seedling', by the following combination of characteristics:

1. 'KORpot033' has dark pink flowers, whereas the 'un-named seedling' has dark red flowers.

2. 'KORpot033' has a flattened convex flower shape, whereas the 'un-named seedling' has a rounded upper flower shape.

The objective of the hybridization was to create a new and distinct rose plant with unique qualities, such as:

1. Compact and uniform growth and flowering under greenhouse conditions when grown as a potted floral plant;
2. Abundant, long lasting, and attractive flowers and foliage;
3. Resistance to diseases encountered in greenhouse and nursery culture; and
4. Suitability for production from softwood cuttings in floral and nursery containers.

This combination of qualities is not present in prior rose cultivars known to the inventor. These objectives have been substantially achieved and in that distinguish 'KORpot033' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORpot033' was selected in April 2010 from the seedling beds to be asexually propagated for further evaluation. The first asexual propagation of 'KORpot033' was done by budding to seedling understocks in June 2010 at the inventor's nursery in Offenseth-Sparrieshoop, Germany.

These initial and other subsequent propagations conducted in controlled environments demonstrate that 'KORpot033' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORpot033'.

DETAILED BOTANICAL DESCRIPTION

The following is a description of 'KORpot033', as observed growing in April 2013 in a nursery in Jackson County, Oreg. on plants of 6 months of age. Color references are made using The Royal Horticultural Society (London, England) Colour Chart, 2001 except where common terms of color are used.

For a comparison, several physical characteristics of the rose variety 'KORbalrom', a rose variety from the same inventor described and illustrated in U.S. Plant Pat. No. 19,025 and issued on Jul. 15, 2008 are compared to 'KORpot033' in Chart 1.

CHART 1

| Characteristic | 'KORpot033' | 'KORbalrom' |
|---|---|---|
| Petal count | Normally 30-35 petals | Normally 75 petals |
| Flower color | Dark pink | Hot pink |
| Stamens | Approx. 50 | Approx. 110 |

Parents:

*Seed parent*.—An 'un-named seedling'.

*Pollen parent*.—An 'un-named seedling'.

Classification:

*Botanical classification*.—*Rosa hybrida* 'KORpot033'.

*Commercial classification*.—Miniature rose.

FLOWER AND FLOWER BUD

Blooming habit: Continuous.

Flower bud:

*Size*.—Upon opening, 28-32 mm in length from base of receptacle to distal end of bud and 14-16 mm diameter at its widest point.

*Bud form*.—Long. High centered.

*Bud color*.—As sepals first unfold, bud color is Red-Purple Group 59A and Red-Purple Group 59B. When ¼ open, the upper surface of petals is Red-Purple Group 61B, and the lower surface is Red-Purple Group 61B. Guard Petals are Red-Purple Group 61A. Some outside petals with intonations of Red-Purple Group 65D in center rib.

*Sepals*.—Color: Upper surface: Yellow-Green Group 144A. Lower surface: Yellow-Green Group 144A. Size: Average 30-35 mm (l)×7-8 mm (w). Shape: Moderate foliaceous appendages on 2 of the five sepals. Apex: Apiculate. Base: Flat at union with receptacle. Quantity: Five. Surface texture: Upper side: Pubescent. Lower surface: Smooth to lightly pubescent. Margins: Pubescent with occasional stipitate glands.

Flower bloom:

*Fragrance*.—None.

*Duration*.—On the plant approximately 12 to 18 days. Senesced petals clinging.

*Size*.—Medium for a miniature rose. When open, the average flower diameter is 65-75 mm and the average flower height is 25-30 mm.

*Form*.—Shape of flower when viewed from the side: Upon opening, upper part: Flat. Upon opening, lower part: Flattened convex. Open flower, upper part: Flattened convex. Open flower, lower part: Flattened convex.

Color:

*Upon opening, petals*.—Outermost petals: Outer Side: Red-Purple Group 60C. Inner Side: Red-Purple Group 61B. Innermost petals: Outer Side: Red-Purple Group 61B. Inner Side: Red-Purple Group N66A.

*Upon opening, basal petal spots*.—Basal petal spot, outermost petals: Outer Side: Green-Yellow Group 1D. Inner Side: Green-Yellow Group 1C. Basal petal spot, innermost petals: Outer Side: Green-Yellow Group 1B. Inner Side: Green-Yellow Group 1A.

*After opening, petals*.—Outermost petals: Outer Side: Red-Purple Group 64B. Inner Side: Red-Purple Group 67A. Innermost petals: Outer Side: Red-Purple Group 61C. Inner Side: Red-Purple Group 67A.

*After opening, basal petal spots*.—Basal petal spot, outermost petals: Outer Side: White Group 155B. Inner Side: Green-Yellow Group 1D. Basal petal spot, innermost petals: Outer Side: White Group 155A. Inner Side White Group 155C.

General tonality: On open flower, Red-Purple Group 61C. No change in the general tonality at the end of the 5$^{th}$ day. Afterwards, general tonality is Red-Purple Group 61B.

Petals:

*Petal count*.—Double.

*Average range*.—Approximately 30-35 petals under normal conditions.

*Petal reflex*.—Petals reflex somewhat.

*Petal edge*.—Emarginate. Slightly undulated.

*Petal shape*.—Obovate. Apex shape is obtuse. Shape of base is attenuate to obtuse.

*Petal size*.—27-30 mm (l)×20-30 mm (w).

*Thickness*.—Thin.

*Petal arrangement*.—Not formal.

*Texture*.—Smooth.

Petaloids:

*Petaloid count*.—Average of 0-6 per flower.

*Petaloid size*.—Petaloids are 15-20 mm (l) and 6-10 mm (w).

*Petaloid color*.—Color of inner side is Red-Purple Group 61C. Color of outer side is Red-Purple Group 61B.

*Petaloid texture*.—Smooth.

*Margins*.—Irregular. Erose.

*Petaloid shape*.—Spatulate. Apex: Obtuse. Base: Attenuate.

Reproductive organs:

*Pistils*.—Abundant. Approximately 40 present. Stigmas: Location: Slightly inferior in position to anthers. Color: Greyed-Yellow Group 160D. Styles: Length: About 6 mm long. Color: Yellow-Green Group 145C.

*Stamens*.—Approximately 50 on average and regularly arranged. Anthers: Size: Average 3 mm (l)×2 mm (w). Pollen: Generally present. Color: Greyed-Yellow Group 160B. Filaments: Color: Yellow-Green Group 150C. Length: 7 mm.

Receptacle:

*Surface*.—Smooth.

*Color*.—Yellow-Green Group 144B.

*Shape*.—Urn-shaped.

*Size*.—10 mm (h)×7 mm (w).

Peduncle:

*Surface*.—With stipitate glands.

*Length*.—35 to 45 mm average length.
*Diameter*.—2 to 3 mm average diameter.
*Color*.—Green Group 138A. Intonations on some peduncles of Greyed-Purple Group 183D.
*Strength*.—Strong.
*Texture*.—Variable. Generally smooth, but many with limited numbers of stipitate glands.
*Borne*.—Variable. Most flowers held solitary. When multiple, generally 2 to 4 flower buds per stem, with the apical bloom being the largest.

THE PLANT

Growth: Moderately vigorous.
Plant habit: Upright to bushy. When grown as a 10 cm pot plant, the average plant height is 25 cm and the average plant width is 14-16 cm.
Stems: Young wood: Green Group 138A. Older wood: Green Group 138A.
*Stem surface texture*.—Young wood: Smooth. Older wood: Smooth.
*Stem color*.—Most stems with intonations of Greyed-Purple Group 183D. Some stems have intonation over 90% of surface.
Prickles: A few. Many stems without prickles.
*Incidence*.—Average of <1 per each 10 cm of stem.
*Size*.—Average length: 3-4 mm.
*Color*.—Immature prickles: White Group N155C. Mature prickles: Orange-White Group 158D.
*Shape*.—Linear.
*Anthocyanin*.—Greyed-Red Group 180D.
Leaves:
*Venation pattern*.—Pyramidal net pattern.
*Leaf size*.—120 mm (l)×85 mm (w).
*Abundance*.—Average.
*Texture*.—Leathery. Upper: Semi-glossy. Lower: Matte.
*Color, mature foliage*.—Upper Leaf Surface: Green Group 137A. Lower Leaf Surface: Green Group 137B.
*Color, juvenile foliage*.—Upper Leaf Surface: Green Group 137A. Lower Leaf Surface: Yellow-Green Group 146B.
*Anthocyanin intonation*.—Greyed-Purple Group 187B on new growth of upper leaflets (both sides and stems).
Leaflets: Normally 5 leaflets on normal leaves in middle of the stem.
*Size*.—Average size of the terminal leaflet is 45-50 mm (l)×25-30 mm (w).
*Shape*.—Overall: Ovate. Base: Obtuse. Apex: Acute.
*Margins*.—Finely serrated.
*Texture*.—Leathery.
*Arrangement*.—Odd pinnate.
*Venation*.—Reticulate.
Stipules:
*Size*.—20 mm long×6 mm wide.
*Stipule color*.—Yellow-Green Group 146A.
*Anthocyanin*.—None observed.
*Stipitate glands*.—Abundant on margins.
*Margins*.—Finely serated.
*Texture*.—Smooth.
*Shape*.—Apex: Apiculate. Base: Flat.
Petiole:
*Length*.—Average 20 mm.
*Diameter*.—Average 3 mm.
*Petiole color*.—Yellow-Green Group 146B.
*Underneath*.—Yellow-Green Group 146B.
*Margins*.—With stipitate glands on upper side.
*Anthocyanin*.—None observed.
*Prickles*.—On underside.
*Stipitate glands*.—Limited on margins.
*Texture*.—Smooth.
Petiole rachis:
*Length*.—Average 25 mm.
*Diameter*.—Average 2 mm.
*Color*.—Yellow-Green Group 146A.
*Margins*.—Stipitate glands. Pubescent on upper side.
*Prickles*.—A few small prickles underneath.
*Stipitate glands*.—Limited numbers of stipitate glands on margins.
Hips/seed formation: None observed.
Winter hardiness: To date, the variety has been grown successfully in Zone 6.
Disease resistance: Good resistance to Powdery mildew (*Sphaerotheca pannosa*) and blackspot (*Diplocarpon rosae*) diseases under normal growing conditions in Jackson County, Oreg.

I claim:

1. A new and distinct variety of rose plant, as described and illustrated herein.

* * * * *

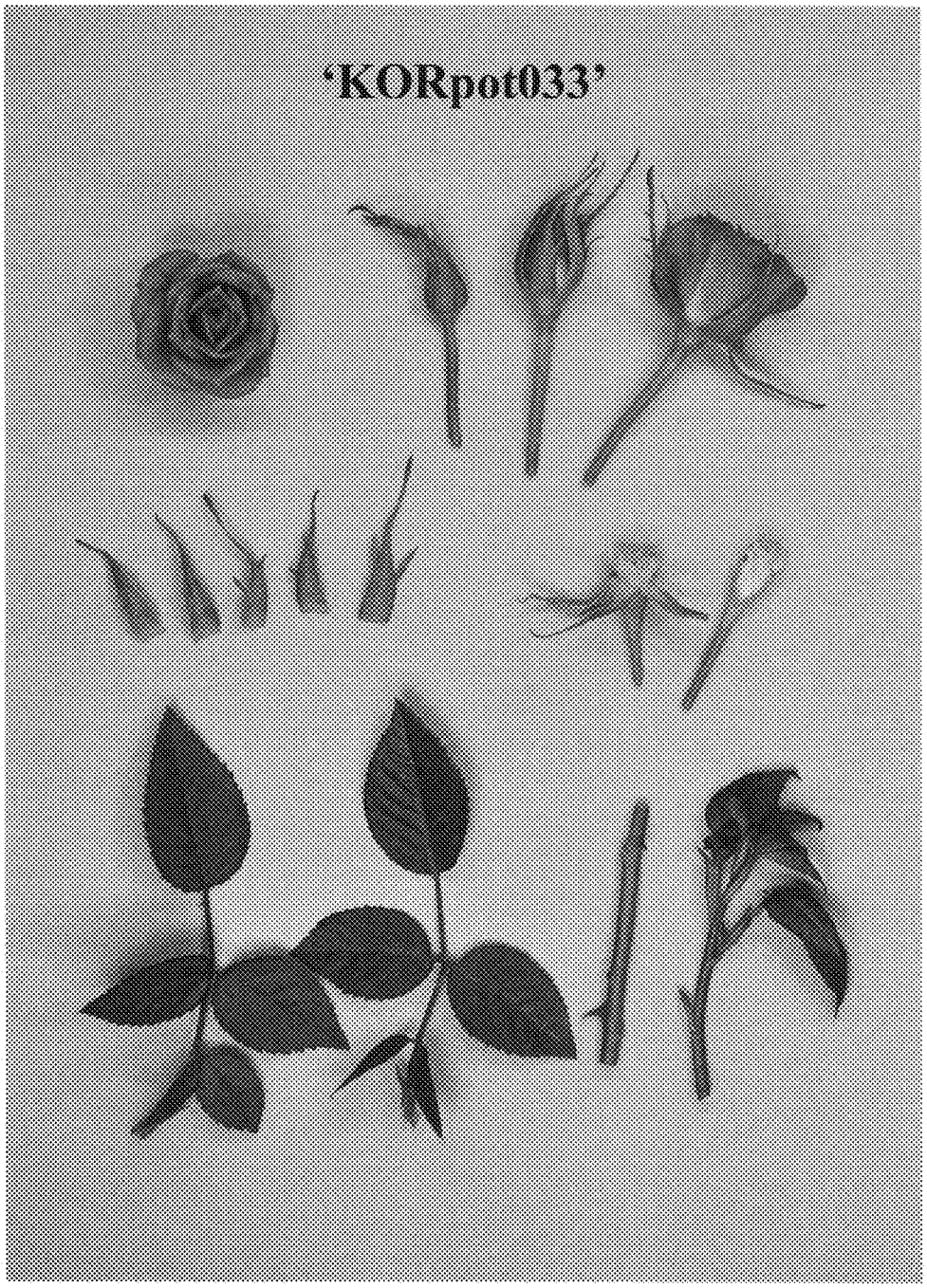
'KORpot033'